United States Patent [19]

Nitta et al.

[11] Patent Number: 4,585,591

[45] Date of Patent: Apr. 29, 1986

[54] 17β-ETHYNYLSTEROIDS AND PROCESS FOR PREPARING SAME

[75] Inventors: Issei Nitta, Machida; Shinichiro Fujimori, Yokohama; Toshio Haruyama, Sagamihara; Shinya Inoue, Yamato, all of Japan

[73] Assignee: Mitsubishi Chemical Industries, Ltd., Tokyo, Japan

[21] Appl. No.: 325,026

[22] Filed: Nov. 25, 1981

[30] Foreign Application Priority Data

| Dec. 10, 1980 [JP] | Japan | 55-174065 |
| Dec. 10, 1980 [JP] | Japan | 55-174066 |
| Feb. 23, 1981 [JP] | Japan | 56-25307 |
| Jul. 28, 1981 [JP] | Japan | 56-118343 |

[51] Int. Cl.$^4$ .................................................. C07J 1/00
[52] U.S. Cl. .............................. 260/397.4; 260/397.45; 260/239.55 C; 260/397.5; 260/397.47
[58] Field of Search ..................... 260/397.4, 397.45

[56] References Cited

U.S. PATENT DOCUMENTS 3,023,206  2/1962  Burn et al. .................... 260/239.55

FOREIGN PATENT DOCUMENTS 845441  8/1960  United Kingdom ............ 260/397.4

OTHER PUBLICATIONS

L. A. van Dijck et al., "Synthesis and Reactions of 3-Methoxy-17-Hydroxy-17-Ethynyl-1,3,5(10)-Estratriene", Recueil Journal of the Royal Netherlands Chemical Society, 96,7-8, Jul.-Aug., pp. 200-205 (1977).

*Primary Examiner*—Elbert L. Roberts
*Attorney, Agent, or Firm*—Oblon, Fisher, Spivak, McClelland & Maier

[57] ABSTRACT

This is disclosed novel intermediates, i.e. 17β-ethynylsteroids, which are useful for the preparation of corticoids such as hydrocortisone and prednisolone, and a process for preparing the same.

4 Claims, No Drawings

17β-ETHYNYLSTEROIDS AND PROCESS FOR PREPARING SAME

BACKGROUND OF THE INVENTION

This invention relates to a novel intermediate for use in the preparation of corticoids (adrenocortical hormones) such as hydrocortisone, prednisolone and the like.

Recently, androst-4-ene-3,17-dione and androsta-1,4-diene-3,17-dione have been produced in a large scale and inexpensively from a sterol such as cholesterol or sitosterol with the aid of bacteria of the Mycobacterium genus whereby various steroidal drugs such as estrone, testosterone, spironolactone, etc. have been produced from these starting compounds.

On the other hand, corticoids which comprises a major portion of the steroidal drugs are still prepared using as an intermediate progesterone which is produced from stigmasterol, or 16-dehydropregnenolone which is produced from diosgenin, or they are prepared from bile acids via a process comprising many steps.

We have carried on investigations with attention to the fact that corticoids can be prepared through fewer steps from the aforementioned androst-4-ene-3,17-dione, androsta-1,4-diene-3,17-dione or androsta-4,9(11)-diene-3,17-dione which has recently be produced inexpensively and in a large scale from 9α-hydroxy-androst-4ene-3,17-dione which has also recently be produced by a fermentative process.

BRIEF DESCRIPTION OF THE PRIOR ART

A novel technique of isomerization of 17α-ethynyl group into 17α-ethynyl group has recently been reported [Tetrahedron Letters, 21, 2665 (1980)].

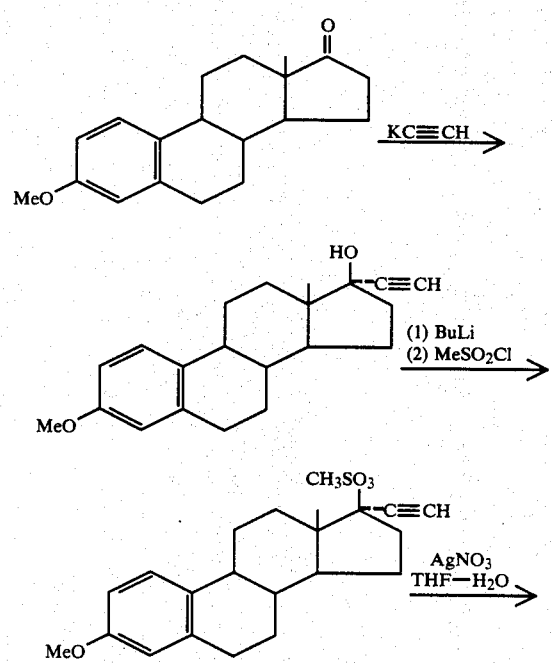

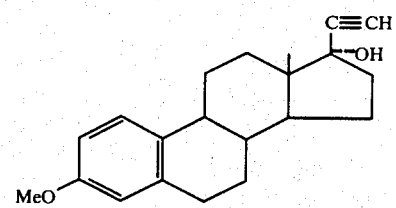

Thus, according to the reported process, estrone methyl ether is ethynylated to give mestranol, which is then esterified with methanesulfonyl chloride. The resulting methanesulfonate ester of mestranol is hydrolyzed in a hydrous tetrahydrofuran solvent in the presence of silver nitrate to give epimestranol (the 17β-ethynyl isomer of mestranol) in an about 80% yield.

This process, however, cannot be said to be advantageous from a commercial viewpoint, since the methanesulfonate ester of a tertiary alcohol such as mestranol methanesulfonic acid ester is extremely unstable and can be synthesized only by limited procedures. For example, according to the procedure described in the above-mentioned article, mestranol is dissolved in tetrahydrofuran and cooled to −60° C. To the cooled solution is added n-butyl lithium in an amount equimolar with the mestranol. Subsequently methanesulfonyl chloride is added also at −60° C. Also regarding the post-treatment, it is suggested in the article that the desired methanesulfonate cannot be obtained in good yield unless the reaction mixture is worked up carefully at a temperature of 0° C. or below.

In addition, in order to prepare 17β-ethynyl-17α-hydroxyandrost-4-en-3-one or 17β-ethynyl-17α-hydroxyandrosta-1,4-dien-3-one which is useful as an intermediates for the preparation of hydrocortisone or prednisolone, it is necessary to synthesize ethisterone methanesulfonic acid ester or 17α-ethynyl-17β-hydroxyandrosta-1,4-dien-3-one 17β-methanesulfonic acid ester. However, in contrast with mestranol, these steroids have a 3-carbonyl group on the ring A of the steroid skeleton, said carbonyl group being sensitive to and reactive with n-butyl lithium. Therefore, the above-mentioned process cannot be employed to synthesize the desired methanesulfonate of such a 3-carbonyl-containing steroid in good yield.

Thus, the above prior art process is considered to be far from satisfactory as a commercial process for the preparation of steroids in that it requires an extremely low temperature of −60° C. and that it is applicable only to those steriods which are free from n-butyl lithium-labile structural element.

SUMMARY OF THE INVENTION

The present invention relates to novel intermediates, i.e., 17β-ethynylsteroids such as, e.g., 17β-ethynyl-17αhydroxyandrost-4-en-3one, 17β-ethynyl-17α-hydroxyandrosta-1,4-dien-3-one, 17β-ethynyl-17α-acetoxyandrosta-1,4-dien-3-one, etc., which are useful for the preparation of corticoids such as hydrocortisone and prednisolone, and a process for preparing the same.

DESCRIPTION OF THE PREFERRED EMBODIMENTS

In one aspect, the present invention provides a 17β-ethynylsteroid of the formula:

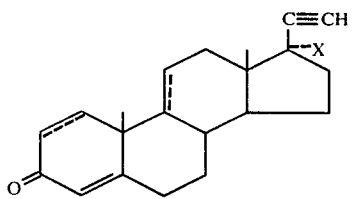

(I)

wherein the dotted lines represented either a single or double bond, and X is hydroxyl or an acyloxy.

The acyloxy group for X contains an acyl moiety having 2 to about 13 carbon atoms, usually 2 to 7 carbon atoms and preferably 2 to 4 carbon atoms.

The compounds of the foregoing formula (I) include 17β-ethynyl-17α-hydroxyandrost-4-en-3-one, 17β-ethynyl-17α-hydroxyandrosta-1,4-dien-3-one, 17βethynyl-17α-hydroxyandrosta-4,9(11)-dien-3-one, 17β-ethynyl-17α-hydroxyandrosta-1,4,9(11)-trien-3-one, etc., as well as esters of these 17β-ethynyl-17α-hydroxysteroids with a carboxylic acid such as acetic acid, propionic acid or benzoic acid.

Thus, the compounds of the formula:

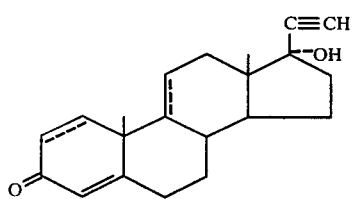

(I')

as well as those of the formula:

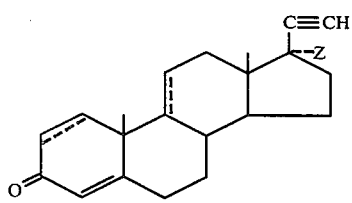

(I'')

are both included in the compounds (I) of this invention. In the above formulas (I') and (I''), the dotted lines are as defined above and Z is an acyloxy group.

The 17β-ethynyl-17α-hydroxysteroids of formula (I') may be prepared by either the following method A or B.

Method A

Steroid having the partial structural formula:

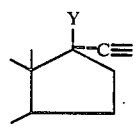

(II)

Cuprous salt →

Steroid having the partial structural formula:

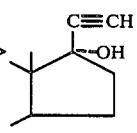

(III)

In formula (II), Y is —ONO₂, —ONO or —OSO₂R where R is an alkyl or aryl group. The alkyl for R usually contains 1 to 10 carbon atoms, preferably 1 to 6 carbon atoms, and the aryl for R usually contains 6 to about 10 carbon atoms.

The steroid having the partial structural formula (II) which is used as a starting compound in this method includes sulfonic acid esters such as 3,3-ethylenedioxy-17αethynyl-17β-hydroxyandrost-5ene 17β-methanesulfonic acid ester, and 3,3-ethylenedioxy-17α-ethynyl-17β-hydroxyandrosta-5,9(11)-diene 17β-methanesulfonic acid ester; nitric acid esters such as 17α-ethynyl-17β-hydroxyandrost-4-en-3-one 17β-nitric acid ester, 17α-ethynyl-17β-hydroxyandrosta-1,4-dien-3-one 17βnitric acid ester and 17α- ethynyl-17β-hydroxyandrosta-4,9(11)-dien-3-one 17β-nitric acid ester, and nitrous acid esters such as 17α-ethynyl-17β-hydroxyandrost-4-en-3-one 17β-nitrous acid ester, 17α-ethynyl-17β-hydroxyandrosta-1,4-dien-3-one 17β-nitrous acid ester and 17α-ethynyl-17β-hydroxyandrosta-4,9(11)-dien-3-one 17β-nitrous acid ester. The steroid skeleton may be a 19-norsteroid such as 19-norethisterone or a steriod the ring A of which comprises an aromatic nucleus such as mestranol. In those steriods having a carbonyl group at the 3-position, the carbonyl group may be protected with an acetal-, enol- or enamine-type protective group. In addition, the steroid may contain one or more substituents such as hydroxyl at the 1-, 6- or 11-position, keto at the 11-position, fluorine at the 6- or 9-position and methyl at the 1-, 6- or 16-position.

The method (Method A) may be carried out by reacting a steroid having the partial structural formula (II) with water in the presence of a catalytic amount of cuprous (i.e. monovalent copper) salt.

The cuprous salt includes cuprous halides such as cuprous chloride, cuprous bromide and cuprous iodide, cuprous cyanide, cuprous oxide, cuprous phosphate, cuprous acetate and the like. Usually cuprous chloride is preferably used because of its inexpensiveness.

The cuprous salt is usually used in an amount of 0.01 to 1.0 mole, preferably 0.05 to 0.4 mole per mole of the starting steroid. The use of much less cuprous salt than above requires a prolonged period of time to attain an adequate conversion of the starting steroid, while the use of much more cuprous salt offers no particular problem.

The reaction is conducted in a solvent which is desirably compatible with water and which desirably has no or little nucleophilicity. Suitable solvents include ethers such as tetrahydrofuran, dioxane and ethylene glycol dimethyl ether, esters such as ethyl acetate, ketones such as acetone, and other highly polar aprotic solvents such as dimethylformamide, and dimethyl sulfoxide.

Usually water should be used in an amount of at least 10 moles per mole of the starting steroid. If much less water is used, an undesirable by-product having the partial structural formula:

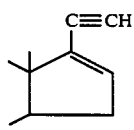

(IV)

will be formed in a significant amount. On the other hand, the use of much more water also involves a problem in that the starting steroid may not completely be dissolved in the medium whereby the reaction does not proceed effectively.

The reaction temperature is usually from −10° C. to 100° C., preferably from 30° C. to 80° C.

Method B

Steroid having the partial structural formula: $\xrightarrow{\text{Ag salt}}$ Steroid having partial structural formula (III)

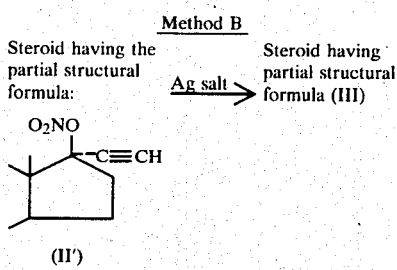

(II')

The steroid nitric acid ester having partial structural formula (II') which is used as the starting compound in this method may be readily prepared from the corresponding 17α-ethynyl-17β-hydroxysteroid by reaction with acetyl nitrate in a manner known per se [see, for example, Tetrahedron, 25, 761 (1969)]. The reaction is carried out by dissolving or suspending the 17α-ethynyl-17β-hydroxysteroid in acetic anhydride and then adding thereto conc. nitric acid dropwise at −20° C. and such procedure can be employed for the commercial preparation.

The steroid nitrate having partial structural formula (II') includes 17α-ethynyl-17β-nitroxyandrost-4-en-3-one, 17α-ethynyl-17β-nitroxyandrosta-1,4-dien-3-one, 17α-ethynyl-17β-nitroxyandrosta-4,9(11)-dien-3-one, 17α-ethynyl-17β-nitroxyester-4-en-3-one, 17α-ethynyl-17β-nitroxyestra-1,4-dien-3-one, mestranol 17β-nitric acid ester and the like. These steroids may be substituted with one or more substituents in a conventional way. For example, the steroids may contain hydroxy at the 1-, 6- or 11-position, keto at the 11-position, fluorine at the 6- or 9-position, methyl at the 1-, 2-, or 16-position and/or a double bond at the 9(11)-position.

The method may be carried out by reacting a steroid nitrate having partial structural formula (II') with water in the presence of a catalytic amount of a silver salt.

The silver salt useful for this purpose includes various silver salts such as silver nitrate, silver perchlorate and silver acetate.

The silver salt is usually used in an amount of 0.05 to 1.5 moles, preferably 0.1 to 1.0 moles and more preferably 0.2 to 0.7 moles per mole of the starting steroid. The use of much less silver salt than above will fail to give a satisfactory conversion of the starting steroid, while the use of much more silver salt involves no particular problem in the reaction itself but is undesirable from an economical viewpoint because of expensiveness of silver.

The type of solvent and the amount of water used in this method are similar to those used in method A. The reaction may be conducted at a temperature of from −10° C. to 70° C., usually from 10° C. to 40° C.

A 17β-ethynyl-17α-acyloxysteroid of formula (I″) may be prepared by reacting a 17β-ethynyl-17α-hydroxysteroid of formula (I′) with an anhydride or halide of a carboxylic acid. Various methods may be employed to effect the reaction.

A first method comprises reacting the 17β-ethynyl-17α-hydroxysteroid of formula (I′) with a carboxylic acid anhydride such as acetic anhydride in an aromatic amine such as pyridine. In this method, the acid anhydride must be used in an amount of at least 1.0 mole, preferably at least 5.0 moles per mole of the starting steroid. The reaction is carried out at a temperature of 80° to 150° C., preferably 100° to 135° C.

In a second method, the steroid of formula (I') is reacted with a carboxylic acid anhydride in a carboxylic acid solvent such as acetic acid. In this case, an acidic compound or a Lewis acid such as p-toluenesulfonic acid, trifluoroacetic acid, sulfuric acid, phosphoric acid, zinc chloride, iron chloride or the like is used as a catalyst. The reaction temperature is usually 0° to 50° C.

A third method is carried out by reacting the steroid of formula (I') with a carboxylic acid anhydride such as acetic anhydride in a conventional solvent such as benzene, toluene, carbon tetrachloride, dichloroethane, etc., in the presence of a pyridine compound such as dimethylaminopyridine as a catalyst. The dimethylaminopyridine catalyst is used in an amount of 1 to 50 mol %, preferably 5 to 10 mol % based on the starting steroid and the acid anhydride should be used in an amount of at least 1.0 mole, preferably at least 5.0 moles per mole of the starting steroid. The reaction temperature is 5° C. to 150° C., preferably 20° to 100° C. In this method, the carboxylic acid formed by the reaction must be neutralized by the addition of a basic substance such as triethylamine, trimethylamine or benzylamine which has a stronger basicity than the pyridine such as dimethylaminopyridine used as a catalyst.

A fourth method comprises reacting the steroid of formula (I') with a carboxylic acid halide such as acetyl chloride in a basic solvent such as pyridine. The acid halide is used in an amount of 1 to 10 moles per mole of the starting steroid. The reaction is carried out at a temperature of 0° to 150° C., preferably 30° to 100° C.

The compounds (I) according to the present invention are useful as intermediates from which corticoids are readily derived, for example, in the following reaction sequence:

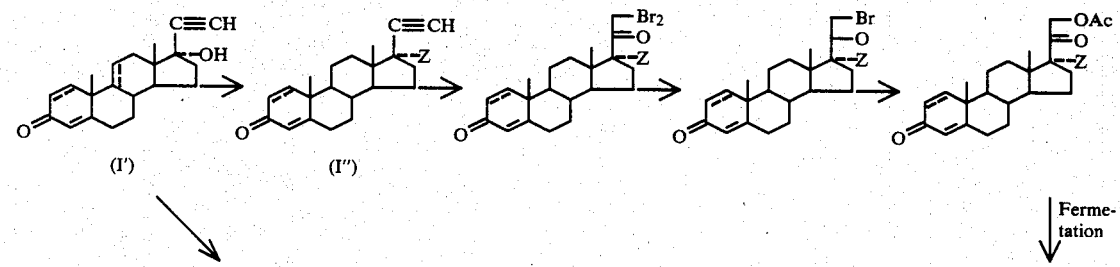

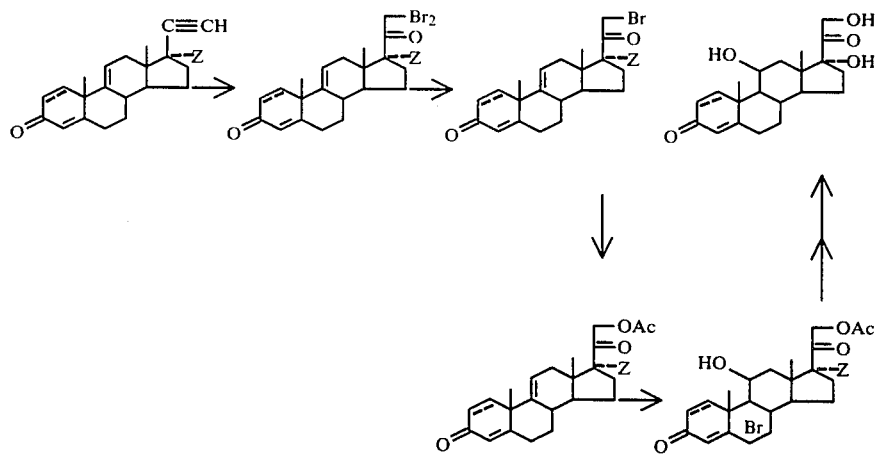

The following examples are given to further illustrate the present invention and it is to be understood that they are not intended to restrict the invention in any way.

EXAMPLE 1

17β-Ethynyl-17α-hydroxyandrosta-1,4-dien-3-one (A) Preparation of the starting 17α-ethynyl-17β-nitroxyandrosta-1,4-dien-3-one To 8.0 g of 17α-ethynyl-17β-hydroxyandrosta-1,4-dien-3-one was added 64 ml of acetic anhydride and the mixture was cooled to −20° C. Thereafter 6.4 ml of fuming nitric acid was added dropwise and stirred for 1 hour at −20° C.

The reaction mixture was poured into 500 g of ice water and stirred. The resulting crystals were filtered off and then dissolved in ethyl acetate. The ethyl acetate solution was washed with water, dried and concentrated to give 8.97 g of 17α-ethynyl-17β-nitroxyandrosta-1,4-dien-3-one. The product could be used as the starting material in the subsequent hydrolysis step without further purification.

(B) Hydrolysis

To 25.0 g of 17α-ethynyl-17β-nitroxyandrosta-1,4-dien-3-one were added 170 ml of tetrahydrofuran, 30 ml of water and 2.0 g of cuprous chloride and the mixture was stirred in a nitrogen atmosphere at 65° C. for 1.5 hours.

To the reaction mixture were added 200 ml of benzene and 200 ml of saturated saline to extract the reaction product into the organic layer. The separated organic layer was washed twice with saturated saline and dried over anhydrous sodium sulfate.

The solvent was distilled off and the residual crystals were recrystallized from a mixture of 250 ml of dichloromethane and 250 ml of n-hexane to give 12.69 g of 17β-ethynyl-17α-hydroxyandrosta-1,4-dien-3-one.

The above crystals were further recrystallized from a mixture of benzene and tetrahydrofuran and then from ethyl acetate to give pure 17β-ethynyl-17α-hydroxyandrosta-1,4-dien-3-one.

Melting point: 218°–219° C.

Specific rotation: $[\alpha]_D^{24} = +90.0°$ (C: 1.02, tetrahydrofuran)

Mass spectrum: 310 (M+)

NMR spectrum: ((CD$_3$)$_2$SO solvent). 18-methyl H, δ 0.91 ppm (3H, S); 19-methyl H; δ 1.21 ppm (3H, S); ethynyl H, δ 2.43 ppm (1H, S).

Referential Example 1

To 0.68 g of 17β-ethynyl-17α-hydroxyandrosta-1,4-dien-3-one as prepared in Example 1 were added 40 ml of benzene, 8 ml of distilled water, 1.12 g of mercuric chloride and 0.2 ml of aniline and the mixture was stirred at 60° C. for 13 hours.

The insoluble matters were filtered off and they were thoroughly washed with chloroform. The chloroform washings were combined with the filtrate (reaction mixture) and the aqueous layer was separated. The organic layer was washed successively with 5% hydrochloric acid and saturated sodium bicarbonate solution and then dried over sodium sulfate. The solvent was then distilled off to give 0.6155 g of 17α-hydroxypregna-1,4-diene-3,20-dione.

Recrystallization from a mixture of 40 ml of tetrahydrofuran and 10 ml of octane gave 0.499 g of purified 17α-hydroxypregna-1,4-diene-3,20-dione. The high speed liquid chromatogram, thin layer chromatogram and infrared absorption, NMR and mass spectra of the product were all in agreement with those of an authentic sample.

EXAMPLE 2

17β-ethynyl-17α-hydroxyandrost-4en-3one (A) Preparation of the starting 17α-ethynyl-17β-nitroxyandrost-4-en-3-one Twenty (20.0) g of ethisterone was suspended in 160 ml of acetic anhydride and cooled to −20° C. To the cooled suspension was added dropwise 16.0 ml of fuming nitric acid and the mixture was stirred for 3 hours at −20° C. The reaction mixture was gradually poured into 20000 g of ice water under stirring. An oily substance which constituted the lower layer was separated and dissolved in 150 ml of ethyl acetate. A portion of the oily substance remained undissolved in ethyl acetate and separated out as crystals, which were then removed by filtration. The removed crystals were ethisterone (2.9 g).

The ethyl acetate layer was washed with saturated saline and dried over magnesium sulfate. The ethyl acetate solvent was then distilled off to give white crystals. The crystals were suspended in 100 ml of n-hexane and then filtered to give 17.3 g of 17α-ethynyl-17β-nitroxyandrost-4-en-3-one.

The product could be used as the starting material in the subsequent hydrolysis step without further purification.

(B) Hydrolysis

The 17α-ethynyl-17β-nitroxyandrost-4-en-3-one (17.3 g, 48.4 mmole) prepared above was dissolved in 173 ml of tetrahydrofuran. Subsequently, 30.0 ml of distilled water and 8.18 g (48.1 mmole) of silver nitrate were added and the mixture was stirred for 24 hours at 23° C., resulting in the formation of white crystals.

To the reaction mixture were added 50 ml of saturated aqueous ammonium chloride solution and 15.0 g of sodium cyanide and the mixture was stirred. After the stirring, the white crystals had disappeared.

Thereafter 150 ml of chloroform was added to extract the reaction product thereinto and the organic layer was washed with water, dried and concentrated to give 14.0 g of white crystals. The crude crystals thus obtained was recrystallized from benzene to give 7.0 g of 17β-ethynyl-17α-hydroxyandrost-4-en-3-one.

The mother liquor of the recrystalization was concentrated to recover another crop of the reaction products, which is then passed through a column filled with silica gel. Elution of the column with benzene gave 2.35 g of pregna-4,16-dien-20-yn-3-one. Subsequently, the column was eluted with benzene-ethyl acetate (10:1) to give 4.1 g of 17β-ethynyl-17α-hydroxyandrost-4-en-3one.

Pure 17β-ethynyl-17α-hydroxyandrost-4-en-3-one was obtained by recrystallization from methanol twice.

Melting point: 201.3°–201.8° C.

Specific rotation: $[\alpha]_D^{21} = +132.7°$ C. (C=1.05, tetrahydrofuran)

Mass spectrum: 312 (M+)

NMR spectrum: (CDCl$_3$ solvent). 18-methyl H, δ 0.91 ppm (3H, SO; 19-methyl H, δ 1.20 ppm (3H, S); ethynyl H, δ 2.48 ppm (1H, S).

EXAMPLE 3

To a mixture prepared by adding 6.2 ml of tetrahydrofuran and 15.8 ml of water to 2.50 g of 17α-ethynyl-17β-nitroxyandrosta-1,4-dien-3-one was added 0.20 g of cuprous chloride, and the resulting mixture was stirred for 4 hours at 65° C. in a nitrogen atmosphere.

Benzene and saturated saline were added to the reaction mixture to extract the product into benzene. The separated benzene layer was further washed three times with saturated saline, dried over anhydrous sodium sulfate and concentrated to give crystals. The high-speed liquid chromatographic analysis of the crystals showed that 17β-ethynyl-17α-hydroxyandrosta-1,4-diene-3-one and 17-ethynylandrosta-1,4,16-trien-3-one were formed in yields of 63 mol % and 32 mol %, respectively.

Comparative Example 1

To 1.25 g of 17α-ethynyl-17β-nitroxyandrosta-1,4-dien-3-one were added 0.10 g of cupric chloride and 10.0 ml o aqueous tetrahydrofuran containing 15% water and the mixture was stirred for 1 hour and 40 minutes at 60° C.

The reaction mixture was worked up in the same manner as described in Example 1(B) to isolate and identify the product. The substance identified was 17α-ethynyl-17β-nitroxyandrosta-1,4-dien-3-one. Thus, the reaction did not proceed in any way.

EXAMPLE 4

(A) Preparation of the starting material, 17α-ethynyl-17β-hydroxyandrost-5-en-3-one 3,3-ethylendioxyacetal 17β-methanesulfonic acid ester To a solution of 1.15 g of 17α-ethynyl-17β-hydroxyandrost-5-en-3-one 3,3-ethylenedioxyacetal in 14.0 ml of dry tetrahydrofuran cooled at −60° C. was added dropwise 2.5 ml (1.56 mmole) of n-butyl lithium solution and the mixture was stirred for 30 minutes. Thereafter 0.5 ml of methanesulfonyl chloride was added dropwise and the stirring at −60° C. was continued for another hour. The temperature was then allowed to rise to room temperature.

The reaction mixture was poured into a mixture of 100 ml of aqueous 20% ammonium chloride and 100 g of ice and then extracted with dichloromethane. The extract was washed with water and dried and the solvent was then distilled off to give 1.48 g of white crystals. The crude crystals were then suspended in 10 ml of diethyl ether, filtered off and dried to give 0.82 g of 17α-ethynyl-17β-hydroxyandrost-5-en-3-one 3,3-ethylenedioxyacetal 17β-methansulfonic acid ester.

(B) Hydrolysis

To 0.67 g of the 17α-ethynyl-17β-hydroxyandrost-5-en-3one 3,3-ethylenedioxyacetal 17β-methanesulfonic acid ester were added 6.0 ml of tetrahydrofuran, 1.0 ml of distilled water and 0.05 g of cuprous chloride and the mixture was stirred for 24 hours at room temperature.

The reaction mixture was extracted with dichloromethane and the separated extract layer was washed with water and dried. The solvent was then distilled off to give 0.52 g of crystals which contain 17β-ethynyl-17α-hydroxyandrost-5-en-3-one 3,3-ethylenedioxyacetal.

The crystals were dissolved in 10.0 ml of acetone and 0.05 g of p-toluenesulfonic acid was added. The mixture was stirred overnight at room temperature.

The reaction mixture was extracted with dichloromethane and the extract was washed with water and dried. Removal of the solvent by distillation gave 0.411 g of white crystals.

The crystals thus obtained were suspended in ethyl acetate and the insoluble crystals were removed by filtration. The removed insoluble crystals were identified as ethisterone (0.04 g).

The ethyl acetate solution (filtrate) was concentrated and the resulting crystals were collected by filtration to give 0.23 g of 17β-ethynyl-17α-hydroxyandrost-4-en-3-one. Repeated recrystallization of the product gave 0.15 g of pure 17β-ethynyl-17α-hydroxyandrost-4-en-3-one.

Melting point: 201.3°–201.8° C.

Specific rotation: $[\beta]_D^{21} = +132.7°$ (C: 1.05, tetrahydrofuran)

Mass spectrum: 312 (M+)

NMR spectrum: (CDCl$_3$). 18-methyl H, δ 0.91 ppm (3H, S); 19-methyl H, δ 1.20 ppm (3H, S); ethynyl H, δ 2.48 ppm (1H, S).

Referencial Example 2

To 1.06 g of 17β-ethynyl-17α-hydroxyandrost-4-en-3-one were added 63 ml of benzene, 13 ml of distilled water, 1.75 g of mercuric chloride and 0.3 ml of aniline and the mixture was stirred at 60° C. for 10 hours.

The insoluble matters were filtered off and the removed insolubles were washed with chloroform several times. The reaction mixture (filtrate) and the washings were combined and the aqueous layer was separated therefrom. The organic layer was washed successively with 5% hydrochloric acid and saturated sodium bicarbonate solution and then dried over sodium sulfate. Thereafter the solvent was distilled off to give 1.04 g of 17α-hydroxypregn-4-ene-3,20-dione.

Recrystallization of the crystals thus obtained from 20 ml of methanol gave 0.53 g of pure 17α-hydroxypregn-4-ene-3,20-dione. The high-speed liquid chromatogram, thin layer chromatogram and NMR, infrared absorption and mass spectra of the product were all in agreement with those of an authentic sample.

EXAMPLE 5

To 0.100 g of 17α-ethynyl-17β-nitroxyandrost-4-en-3-one were added 3.0 ml of tetrahydrofuran, 0.5 ml of distilled water and 0.008 g of silver nitrate and the mixture was stirred for 24 hours at room temperature. A mixture of 0.100 g of sodium cyanide in 10 ml of aqueous saturated ammonium chloride solution was then added and the reaction mixture was extracted with dichloromethane.

The high-speed liquid chromatographic analysis of the separated dichloromethane solution showed that 17β-ethynyl-17α-hydroxyandrost-4-en-3-one, pregna-4,16-dien-20-yn-3-one and 17α-ethynyl-17β-nitroxyandrost-4en-3-one were obtained in yields of 72 mol %, 12 mol % and 9 mol %, respectively.

EXAMPLE 6

17α-Ethynyl-17β-nitroxyandrosta-1,4-dien-3-one (2.5 g) as prepared in Example 1(A) was dissolved in 17 ml of tetrahydrofuran. Subsequently 3.0 ml of distilled water and 0.55 g of silver nitrate were added and the mixture was stirred for 24 hours at 25° C.

The reaction mixture was poured into 70 ml of saturatedammonium chloride solution containing 0.70 g of sodium cyanide. After stirring for 15 minutes, the reaction mixture was extracted with dichloromethane and the separated organic layer was washed with water and dried to give 2.40 g of white crystals.

The crude crystals thus obtained was recrystallized from a mixture of 20 ml of tetrahydrofuran and 140 ml of n-hexane to give 1.10 g of 17β-ethynyl-17β-hydroxyandrosta-1,4-dien-3-one.

Recrystallization from ethyl acetate twice gave pure 17β-ethynyl-17α-hydroxyandrosta-1,4-dien-3-one.

Melting point: 218°–219° C.

Specific rotation: $[\alpha]_D^{24} = +90.9°$ (C: 1.02 tetrahydrofuran)

Mass spectrum: 310 (M+)

NMR spectrum: ((CD$_3$)$_2$SO). 18-methyl H, δ 0.91 ppm (3H, S); 19-methyl H, δ 1.21 ppm (3H, S); ethynyl H, δ 2.43 ppm (1H, S).

EXAMPLE 7

To 12.0 g of 17β-ethynyl-17α-hydroxyandrosta-1,4-dien-3-one were added 50 ml of pyridine and 50 ml of acetic anhydride and the mixture was heated at 120° C. for 30 hours. The reaction mixture was poured into ice water and the separating tarry substance was extracted into dichloromethane. The organic layer was washed successively with 5% hydrochloric acid and 5% sodium bicarbonate solution and the separated organic layer was dried over anhydrous sodium sulfate and concentrated. The concentrate was passed through a column filled with 250 g of alumina and eluted with 500 ml of a mixture of benzene and ethyl acetate (9:1) to give 12.3 g of crystals. Recrystallization of the crystals from octane-tetrahydrofuran (20:1), heptane-ethanol (5:1) and octane-tetrahydrofuran (30:7) gave 8.1 g of 17β-ethynyl-17β-acetoxyandrosta-1,4-dien-3-one, m.p. 171.8°–172.6° C. (rate of temperature elevation: 1° C./min.).

NMR spectrum (CDCl$_3$): δppm. 1.00 (S, 3H), 1.26 (S, 3H), 2.02 (S, 3H), 2.56 (S, 1H), 6.04 (S, 1H), 6.15 (q, 1H), 6.98 (d, 1H).

EXAMPLE 8

To 2.0 g of 17β-ethynyl-17α-hydroxyandrosta-1,4-dien-3-one were added 2.0 ml of acetic anhydride, 2.0 ml of triethylamine, 0.114 g of dimethylaminopyridine and 5.0 ml of toluene and the mixture was heated at 80°–90° C. for 11 hours. Upon cooling, the reaction product was extracted into dichloromethane in the same manner as described in Example 7. The liquid chromatographic analysis of the extract showed that 17β-ethynyl-17α-acetoxyandrosta-1,4-dien-3-one was formed in a 96.7 mol % yield.

EXAMPLE 9

To 2.0 g of 17β-ethynyl-17α-hydroxyandrosta-1,4-dien-3-one were added 10.0 ml of acetic acid, 4.0 ml of acetic anhydride and 0.4 g of zinc chloride and the mixture was stirred for 25 hours at room temperature. The reaction product was extracted into dichloromethane in the same way as described in Example 7. The liquid chromatographic analysis of the extract showed that 17β-ethynyl-17α-acetoxyandrosta-1,4-dien-3-one was formed in a 77.2 mol % yield.

What is claimed is:

1. A method for preparing a 17β-ethynylsteroid having the partial structural formula:

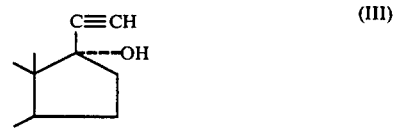

(III)

which comprises subjecting a steroid having the partial structural formula:

(II)

wherein Y is —ONO$_2$, —ONO or —OSO$_2$R where R is an alkyl or aryl,
to hydrolysis in the presence of a cuprous salt.

2. A method for preparing a 17β-ethynylsteroid having the partial structural formula:

(III)

which comprises subjecting a steroid having the partial structural formula:

to hydrolysis in the presence of a silver salt.

3. A method as claimed in claim 1 or 2 wherein said 17β-ethynylsteroid having the partial structural formula (III) is a compound of the formula:

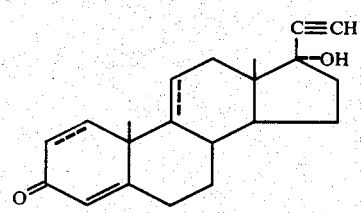 (I')

wherein the dotted lines represent either a single or double bond, and said steroid having the partial structural formula (II) or (II') is a compound of the formula:

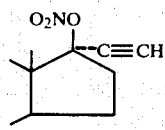 (II')

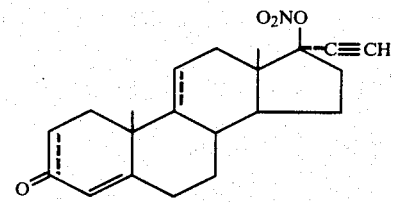 (I-a)

wherein the dotted lines are as defined above.

4. A method for preparing an acyloxysteroid which comprises reacting a 17β-ethynyl-17α-hydroxysteroid of the formula:

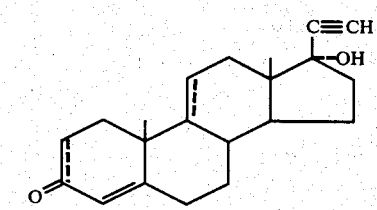 (I')

wherein the dotted lines represent either a single or double bond.

with a carboxylic acid anhydride or halide to give a 17β-ethynyl-17α-acyloxysteroid of the formula:

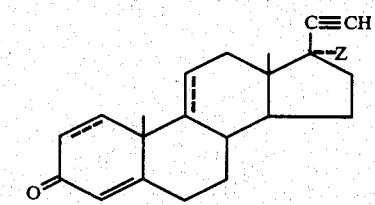 (I'')

wherein the dotted lines are as defined above and Z is an acyloxy.

* * * * *